United States Patent [19]

Jakob et al.

[11] Patent Number: 5,166,426
[45] Date of Patent: Nov. 24, 1992

[54] PROCESS FOR PRODUCING L-CARNITINE FROM D,L-CARNITINE NITRILE SALTS

[75] Inventors: Harald Jakob, Hasselroth; Klaus Huthmacher, Gelnhausen; Herbert Klenk, Hanau, all of Fed. Rep. of Germany

[73] Assignee: Degussa AG, Frankfurt am Main, Fed. Rep. of Germany

[21] Appl. No.: 858,492

[22] Filed: Mar. 27, 1992

[30] Foreign Application Priority Data

Apr. 12, 1991 [DE] Fed. Rep. of Germany ....... 4111913

[51] Int. Cl.$^5$ ............................................. C07C 229/00
[52] U.S. Cl. ..................................... 562/567; 548/535
[58] Field of Search ......................... 562/567; 548/535

[56] References Cited

U.S. PATENT DOCUMENTS 3,488,729 1/1970 Jakob et al. .
4,914,208 4/1990 Jakob et al. .

FOREIGN PATENT DOCUMENTS 0157315 10/1985 European Pat. Off. .
0312726 4/1989 European Pat. Off. .
62-286959 12/1987 Japan .

OTHER PUBLICATIONS

An English language abstract of JP 62-286969 (including Chemical Abstract 109: 73908f) Jun. 6, 1989.
Strack, E., et al., "Die Darstellung von L–Carnitin und seiner Isomeren", *Z. physiol. Chem.* (1960), vol. 318, pp. 129–137, vol. 51, pp. 283–290.

*Primary Examiner*—Michael L. Shippen
*Attorney, Agent, or Firm*—Beveridge, DeGrandi & Weilacher

[57] ABSTRACT

Synthesis of L-carnitine by chemical optical resolution of D,L-carnitine nitrile salts, where the D,L-carnitine nitrile salt is reacted with optically active N-acetylproline as the resolving agent in order to form the diastereomer salts after conversion to the hydroxide form, one of the two diastereomer salts is separated by fractional crystallization and the fraction containing mainly L-carnitine nitrile salt is treated with an optically inactive strong acid in order to split off the optically active N-acetylproline and then the resolving agent is separated and the resulting L-carnitine nitrile salt is saponified to L-carnitine. N-acetyl-L-proline is used as the resolving agent and the diastereomer (LL) salt is obtained in crystalline form in a high optical purity by fractional crystallization and the L-carnitine nitrile salt obtained after splitting off and separating N-acetyl-L-proline is used directly for saponification without further crystallization.

16 Claims, No Drawings

PROCESS FOR PRODUCING L-CARNITINE FROM D,L-CARNITINE NITRILE SALTS

BACKGROUND AND INTRODUCTION

The present invention concerns a process for producing L-carnitine by classical chemical optical resolution of D,L-carnitine nitrile salts using optically active N-acetylproline as the resolving agent and saponifying the resulting L-carnitine nitrile salt.

L-Carnitine is also known as vitamin $B_T$ and is being used increasingly in dietetic and pharmaceutical preparations for treatment of myocardial damage, chronic circulation disorders and to increase energy levels. Most chemical methods of synthesizing L-carnitine include chemical optical resolution of a racemic carnitine precursor. Resolution of the precursor D,L-carnitinamide chloride using an optically active acid (East German Patent 23,217, German Patents (OLS) 2,927,672 and 3,342,713) is known. A disadvantage of this process is especially the fact that D,L-carnitinamide chloride must first be synthesized from D,L-carnitine nitrile chloride. In comparison with resolution at the level of D,L-carnitine nitrile chloride, which can be saponified directly to carnitine, an additional step is thus necessary.

Resolution at the level of the carnitine precursor D,L-3-chloro-2-hydroxypropyltrimethylammonium chloride is known but is not completely satisfactory on an industrial scale (see European Patents A 157,315 and A 312,726).

Common features of resolution of D,L-carnitine nitrile salts such as D,L-carnitine nitrile chloride (which is synthesized in general by cyanidation of D,L-3-chloro-2-hydroxypropyltrimethylammonium chloride or D,L-epoxypropyltrimethylammonium chloride) include the conversion of the chloride to the hydroxide, reaction with an optically active acid, separation of the diastereomer salts and cleavage thereof with a strong acid, where the optically active carnitine nitrile salt is obtained and the starting optically active acid is recovered.

For example, D-tartaric acid and D-camphor-10-sulfonic acid have been proposed as optically active acids for resolution of carnitine nitrile chloride, but they necessitate frequent recrystallization of the diastereomer salts because of the low differences in solubility. An improvement was achieved by a combined use of D-camphor-10-sulfonic acid and dibenzoyl L-tartaric acid (E. Strack et al., *Z. physiol. Chem.* 318, 129 (1960)), but two resolving agents make the process expensive and unsuitable for industrial use. When only dibenzoyl L-tartaric acid is used, the difference in solubility between the two diastereomers is low and this in turn has a negative effect on yield.

Use of optically active N-acetylglutamic acid as the acidic resolving agent is also known for resolution of D,L-carnitine nitrile salts (Japanese Patent 43-8248, Dutch Patent A 6,614,321). In this optical resolution, it is not the naturally occurring N-acetyl-L-glutamic acid that is necessary but instead its antipode N-acetyl-D-glutamic acid which is not itself available in adequate amounts or must be synthesized by means of D-carnitine nitrile chloride. However, when N-acetyl-L-glutamic acid is used as the resolving agent and the insoluble salt of D-carnitine nitrile and N-acetyl-L-glutamic acid is first separated from the diastereomer mixture, production of an optically pure L-carnitine-N-acetyl-D-glutamate from the mother liquor requires multiple fractional crystallization which entails a considerable loss of yield.

In order to improve the efficiency of the aforementioned resolution and increase the optical purity of the desired L-carnitine nitrile salt, Japanese Patent A 62-286959 (1987) proposes first subjecting the mixture of diastereomer salts to fractional crystallization, then exchanging the optically active anion of the crude diastereomer containing mainly L-carnitine nitrile with an optically inactive acid anion (especially perchlorate or oxalate), and then purifying the resulting salt by means of further fractional crystallization. However, the cost of the process is greatly increased by this second fractional crystallization step. Furthermore, the yield is reduced especially by resolution on a production scale and this leads to higher costs for use and recovery of the optically inactive acid to be selected.

Japanese Patent 62-286959 mentions optically active N-acetylproline in addition to numerous other cleavage reagents but does not mention whether this acid should be used in the L or D form. In view of the practical example using N-acetyl-L-glutamic acid, where L-carnitine nitrile N-acetyl-L-glutamate is more difficult to crystallize than the (DL) salt and thus necessitates the second fractional crystallization step, those skilled in the art could have expected comparable results when using N-acetyl-L-proline that is readily accessible from naturally occurring raw materials, namely L-proline.

In the process according to German Patent Application P 40 15 573.0, optically active N-acetyl-2,2,5,5-tetraalkylthiazolidine-4-carboxylic acids are used as resolving agents for resolution of D,L-carnitine nitrile chloride. However, these resolving agents are accessible only by synthesis and they also require classical chemical optical resolution.

SUMMARY OF THE INVENTION

An object of the present invention is to provide a process for producing L-carnitine that will include resolution of a D,L-carnitine nitrile salt and saponification of the resulting L-carnitine nitrile salt. A resolving agent that occurs in a sufficient amount in the optically active form and which has optionally been chemically modified by a central method should be used for resolution. Furthermore, the diastereomer containing L-carnitine nitrile should be almost insoluble in resolution and should be obtained in a high optical purity and high yield, thus making a second fractional crystallization superfluous.

According to the present invention, this and other objects are achieved by producing L-carnitine by optical resolution of D,L-carnitine nitrile salts, where the D,L-carnitine nitrile salt is reacted with optically active N-acetylproline as the resolving agent in order to form the diastereomer salts after conversion to the hydroxide form. One of the two diastereomer salts is then separated by fractional crystallization and the fraction containing mainly L-carnitine nitrile salt is treated with an optically inactive strong acid in order to split off the optically active N-acetylproline. Then the resolving agent is separated and the resulting L-carnitine nitrile salt is saponified to L-carnitine.

A feature of the present invention is that N-acetyl-L-proline is used as the resolving agent and the diastereomer (LL) salt is obtained in crystalline form in a high optical purity by fractional crystallization and the L- carnitine nitrile salt (obtained after splitting off and separating N-acetyl-L-proline) is used directly for saponification without further crystallization.

DETAILED DESCRIPTION OF THE INVENTION

In the process according to the present invention, a salt of the D,L-carnitine nitrile cation and the anion of an optically inactive acid (often D,L-carnitine nitrile chloride due to the production process) is converted by a known method to the hydroxide form, i.e., D,L-3-cyano-2-hydroxypropyltrimethylammonium hydroxide. Especially strong basic organic or inorganic ion exchangers in the OH⁻ form or electrodialysis are suitable for this purpose. D,L-Carnitine nitrile hydroxide is preferably reacted with N-acetyl-L-proline in aqueous solution, forming the diastereomer (DL) and (LL) salts. The molar ratio of D,L-carnitine nitrile hydroxide to N-acetyl-L-proline is preferably about 1:1, but it is also possible to select a molar ratio between 1:0.5 and 1:1 when also using an optically inactive organic carboxylic acid such as especially acetic acid, where the molar ratio of D,L-carnitine nitrile hydroxide to the sum of N-acetyl-L-proline and the organic optically inactive carboxylic acid is again about 1:1. The molar ratio can, of course, be varied so long as sufficient amounts of reactants are used to enable formation of the desired product, as will be apparent to those skilled in the art.

After formation of the diastereomer salt mixture and dehydration of the mixture by distillation under reduced pressure and/or azeotropic distillation with a suitable organic solvent, the diastereomer salts are separated from each other by fractional crystallization using organic solvents.

The diastereomer salts with the N-acetyl-L-proline anion have considerable differences in solubility and permit easy separation of the diastereomers. Surprisingly, the diastereomer (LL) salt (L-carnitine nitrile N-acetyl-L-prolinate) is less soluble than the (DL) salt and therefore can be obtained as a crystal line product in high optical purity and high yield. After separating the crystal line product from the mother liquor containing the diastereomer (DL) salt (D-carnitine nitrile-N-acetyl-L-proline), the (LL) salt is recrystallized if desired. For example, over 90% yield can be obtained with over 95% purity.

Preferred solvents for fractional crystallization of the diastereomer salt pairs include ($C_1$–$C_6$) alcohols, especially ($C_1$–$C_4$) alcohols; ($C_3$–$C_7$) ketones such as especially acetone and methyl isobutyl ketone (MIBK); cyclic ethers, such as tetrahydrofuran and dioxane; alkylene glycol ethers with 3 to 7 carbons, especially ethylene glycol monomethyl ether or mixtures of such solvents. An especially preferred procedure for separation of the diastereomers consists of dissolving the anhydrous diastereomer mixture in a primary $C_3$ to $C_5$ alcohol, especially n-butanol, and then precipitating the insoluble (LL) salt by adding a ketone, especially acetone. n-Butanol and acetone are used in a volume ratio of 1:1 to 1:4, especially 1:2.5 to 3.5, to crystallize the (LL) salt out of the diastereomer mixture. To increase the optical purity, the crystallized and separated (LL) salt can also be washed, preferably with acetone or methyl isobutyl ketone and/or recrystallized if necessary, preferably using the same solvents as in separation of the diastereomer. n-Butanol and acetone are preferably used in a volume ratio of 1:1.5 to 2.5 for recrystallization.

The (LL) salt is treated with a strong optically inactive acid in a known manner in order to split off the N-acetyl-L-proline from the diastereomer (LL) salts and recover the resolving agent. According to a preferred embodiment, an aqueous solution of the (LL) salt is first treated with a cation exchanger in the H⁺ form and then N-acetyl-L-proline is separated by means of water from the cation exchanger loaded with L-carnitine nitrile. Finally, the L-carnitine nitrile salt of this acid is eluted by means of an optically inactive strong acid, especially a mineral acid, preferably hydrochloric acid. The eluate contains the L-carnitine nitrile salt of the optically inactive acid and can be used directly without further purification or crystallization of the L-carnitine nitrile salt for saponification to form L-carnitine by known methods. In this embodiment, the resolving agent can be recovered almost completely (more than 96%) even on a commercial production scale.

As an alternative, although a less preferred alternative, the diastereomer (LL) salt can be reacted directly with an optically active strong acid in a molar ratio of 1:1. Then the N-acetyl-L-proline is extracted from the reaction mixture that has been freed of water by using a suitable organic solvent such as acetone or a solvent mixture such as acetone/ethanol, where the L-carnitine nitrile salt of the optically inactive acid that is used remains as a residue and is sent for saponification.

Of course, as a rule, the mother liquor containing the diastereomer (DL) salt from separation of the diastereomers and mother liquor from recrystallization for recovering the cleavage reagent are usually treated as described above.

The L-carnitine nitrile salts are converted to L-carnitine in a known manner by heating them with mineral acid, especially hydrochloric acid, and then separating the anion of the mineral acid from the resulting L-carnitine salt, preferably using anion exchangers.

Use of N-acetyl-L-proline as a resolving agent makes it possible to separate the (LL) salt in a surprisingly optically pure crystalline form and in a high yield. A second fractional crystallization step is thus superfluous. Furthermore, the resolving agent can be recovered almost completely, usually in an amount between 97% and 99.5%. Starting from (DL)-carnitine nitrile chloride, L-carnitine is accessible in a yield of more than 70% and with a high enantiomer purity by the process according to the present invention.

EXAMPLES

EXAMPLE 1

Optical resolution of D,L-carnitine nitrile chloride with L-N-acetylproline a) Forming the diastereomer salts and separating the (LL) salt 1 mol of an approximately 6 wt % aqueous D,L-carnitine nitrile hydroxide solution was adjusted to a pH of 5.5 by adding 158.2 g (1.006 mol) L-N-acetylproline (L-NAP, $[\alpha]_d^{20} = -116°$ C. = 1, $H_2O$) and the solution, which assumed a faint yellow color was then concentrated in vacuo at 60° C. The residue (336 g yellow oil) was dissolved in 250 ml n-butanol and distilled in a partial vacuum (bottom temperature 70° C.) through a water separator (about 30 ml aqueous phase) in order to achieve complete dehydration. This yielded a solution that was mixed with 750 ml acetone at the boiling point. When left to cool to room temperature, the solution began to crystallize. The suspension was stirred for 2 more hours at room temperature, the precipitate was filtered by suction and washed with acetone. The pair of crude salts still containing some acetone was then mixed with 200 ml n-BuOH in order to avoid recrystallization and then the mixture was heated while distilling off the remaining acetone (about 35 ml). At about 100° C., the solids began to dissolve and the solution boiled so 400 ml acetone were added slowly, forming a precipitate. After standing at room temperature, stirring was continued for 2 hours at this temperature. Then the solids were filtered by suction, washed with acetone and dried at 70° C. in vacuo.

117.0 g (0.391 mol; 78.2% of the theoretical) colorless (LL) salt was formed.

Analysis calculated for $C_{14}H_{25}N_3O_4$ (299.37): C 56.17 H 8.42 N 14.04; found C 56.01 H 8.55 N 14.23.

$[\alpha]_D^{20} = -69.4°$ (c=1, water).

b) Cleavage of the diastereomer (LL) salt 104.8 g (0.35 mol) (LL) salt were dissolved in about 900 ml water and pumped through a glass column packed with 0.5 l of Lewatit SP 112/H+ form ion exchange resin (dwell time: 2 hours). The pH in the eluate dropped to 1.8 and then slowly rose again in the remaining course of elution with water. The eluates up to a pH of 3.3 were combined for determination of concentration by titration (0.1N NaOH) and concentrated in vacuo and the remaining residue was dried in vacuo at 75° C.

54.8 g (0.349 mol); 99.6%) faintly colored L-N-acetylproline $[\alpha]_D^{20} = -115.8°$ (c=1, water)

The ion exchange column was eluted with 10% hydrochloric acid after rinsing with water to a pH of 4 to 5. Hydrochloric acid was pumped through the column until no carnitine nitrile chloride could be detected in the eluate with Reinecke's salt.

By diluting with hydrochloric acid, the ion exchange resin was regenerated again for the next salt pair separation after being rinsed with water.

c) Separation of the diastereomer (DL) salt

In order to remove the organic solvents the combined mother liquors of the (LL) salt precipitation and recrystallization were first distilled at normal pressure up to 70° C. (acetone) in order to remove the organic solvents and then were distilled in a partial vacuum (n-BuOH). The oily residue was dissolved in 1500 ml water and stripped in vacuo to remove the remaining butanol. The lightly colored solution was pumped through the strongly acidic ion exchanger described above in order to separate the salt pairs. The eluate (pH 3.3-content monitored by titration) was rotated and dried in vacuo at 70° C.: 93.0 g (0.592 mol; 96.2%) weakly colored L-N-acetylproline.

$[\alpha]_D^{20} = -115.8°$ (c=1, water)

The total recovery of the L-N-acetylproline thus amounted to 97.4%.

In the recycling operation, the aqueous L-NAP eluates were combined, concentrated and returned to the resolution process as an aqueous approximately 13% solution (solubility of L-NAP in water at room temperature: 16%).

d) Saponification of L-carnitine nitrile chloride and isolation of L-carnitine

The hydrochloric acid L-carnitine nitrile chloride eluates from the (LL) salt cleavage were rotated until dry in vacuo, the oily crystalline residue was mixed with 120 g 37% hydrochloric acid (1.23 mol) and saponified under standard conditions. After cooling to 5° C., the precipitated ammonium chloride was filtered out and rewashed with cold concentrated HCl. The filtrate was centrifuged in vacuo to dryness. The oily crystalline residue was dissolved in 300 ml water and pumped through a glass column packed with 0.5 l of Amberlite IRA 410/OH− form. The clear solution was then concentrated, the residue was dissolved in 125 ml n-BuOH and heated on a water separator in a partial vacuum in order to achieve complete dehydration. A crystalline precipitate had already formed. At the boiling point, 125 ml acetone were added and stirring was continued for 30 minutes at reflux. After cooling to 20° C., stirring was continued for 1 hour, the precipitate was filtered by suction, washed with acetone and dried at 75° C. in vacuo:

51.0 g (0.316 mol) colorless L-carnitine (90.2% based on the (LL) salt). $[\alpha]_D^{20} = -31.7°$ (c=1, water) HPLC:content>99%.

EXAMPLE 2

Forming the diastereomer salts of D,L-carnitine nitrile hydroxide with L-N-acetylproline and acetic acid 0.5 mol of an approximately 6% D,L-carnitine nitrile hydroxide solution was mixed with 47.15 g (0.3 mol) L-N-acetylproline and 12 g (0.2 mol) acetic acid, yielding a faintly colored solution with a pH of 6. After concentrating the salt solution in vacuo, 155.3 g of an oil that is be mixed with 125 ml n-butanol and is distilled off in a partial vacuum over a water separator in order to achieve complete dehydration in the partial vacuum (25 ml aqueous phase). 375 ml acetone were added at the boiling point to the residue. When the solution was left to cool, a crystalline precipitate formed and was heated in 100 ml n-BuOH after suction filtration and washing with acetone. During the distillation of acetone, the precipitate went into solution at about 100° C. Next 200 ml acetone were added at the boiling point and crystallization began. After cooling to 20° C., stirring was continued for 2 additional hours, the precipitate was filtered by suction, washed with acetone and dried at 75° C. in vacuo:

51.5 g (0.172 mol; 68.8% of the theoretical) colorless (LL) salt.

Investigation of the diastereomer salt with the Chira monitor (HPLC) yielded 96.9% enantiomeric excess (ee) for the L-carnitine nitrile content in the salt.

15 g (50 mmol) (LL) salt were dissolved in water and adjusted to a pH of 2 with hydrochloric acid. Then the solution was evaporated to dryness and the residue was dissolved in ethanol. This procedure was performed again and the residue was stirred with 50 ml acetone. The insoluble L-carnitine nitrile chloride was filtered by suction and washed with acetone. After drying, 8.5 g (47.6 mmol; 95.2% based on the LL salt) L-carnitine nitrile chloride with an optical rotation of $[\alpha]_D^{20} = -26.4°$ (c=1, water) were obtained.

EXAMPLE 3

Resolution was performed according to Example 1, but 120 moles D,L-carnitine nitrile chloride were used instead. To separate the crude (LL) salt, 250 ml n-butanol were used per mol of the diastereomer salts and 750 ml acetone for precipitation purposes. Recrystallization was performed with 200 ml n-butanol per mol salt and then 400 ml acetone were used for precipitation. Yield of pure (LL) salt: 52.3 mol; 87.2% of the theoretical; enantiomeric purity of the L-carnitine nitrile chloride, determined by measuring the salt on a Chira monitor (HPLC, external standard): 96.8% ee. When the (LL) salt was separated according to Example 1b, 96.9% of the starting N-acetyl-L-proline was recovered. The hydrochloric acid L-carnitine nitrile chloride eluates were converted to L-carnitine according to Example 1d.

Further variations and modifications of the invention will become apparent to those skilled in the art from the foregoing and are intended to be encompassed by the claims appended hereto.

German Priority Application P 41 11 913.4, filed on Apr. 12, 1991, is relied on and incorporated by reference.

What is claimed:

1. A process for producing L-carnitine by optical resolution of D,L-carnitine nitrile salts, said process comprises:
    (a) converting D,L-carnitine nitrile salt to D,L-carnitine nitrile hydroxide,
    (b) reacting said D,L-carnitine nitrile hydroxide with N-acetyl-L-proline as the optically active resolving agent to form a mixture of LL and DL diastereomer salts,
    (c) separating said LL diastereomer salt from said DL diastereomer salt by fractional crystallization using organic solvents, wherein said fractional crystallization is the sole fractional crystallization,
    (d) splitting said LL diastereomer salt to produce said resolving agent and L-carnitine nitrile salt and separating said resolving agent from said L-carnitine nitrile salt, and
    (e) saponifying said L-carnitine nitrile salt to form L-carnitine.

2. The process according to claim 1, wherein in said step (b) the ratio of said D,L-carnitine nitrile hydroxide to said N-acetyl-L-proline is about 1:1.

3. The process according to claim 1, further comprising utilizing an optically inactive carboxylic acid in step (b) and wherein the ratio of said N-acetyl-L-proline and said optically inactive carboxylic acid to said D,L-carnitine nitrile hydroxide is between 1:0.5 and 1:1.

4. The process according to claim 3, wherein said optically inactive carboxylic acid is acetic acid.

5. The process according to claim 1, wherein said organic solvent in step (c) is at least one member of the group consisting of ($C_1$-$C_6$) alcohols, ($C_3$-$C_7$) ketones, cyclic ethers, ($C_3$-$C_7$) alkylene glycol ethers, and mixtures thereof.

6. The process according to claim 5, wherein said organic solvent is at least one member of the group consisting of ($C_1$-$C_4$) alcohols, acetone, methyl isobutyl ketone, tetrahydrofuran, dioxane, ethylene glycol monomethyl ether, and mixtures thereof.

7. The process according to claim 1, wherein said step (c) comprises dissolving said LL and DL diastereomer salts in a primary $C_3$ to $C_5$ alcohol and then precipitating said LL diastereomer salt by adding a ketone.

8. The process according to claim 7, wherein said alcohol is n-butanol and said ketone is acetone and the volume ratio of said n-butanol: said acetone is 1:1 to 1:4.

9. The process according to claim 8, wherein said ratio is 1:2.5 to 3.5.

10. The process according to claim 7, further comprising washing and/or recrystallizing said LL diastereomer salt.

11. The process according to claim 1, wherein said step (d) comprises treating said LL diastereomer salt with a cation exchanger, separating said N-acetyl-L-proline by means of water from said cation exchanger, and eluting said LL diastereomer salt by means of an optically inactive strong acid.

12. The process according to claim 11, wherein said acid is a mineral acid.

13. The process according to claim 12, wherein said acid is hydrochloric acid.

14. The process according to claim 1, wherein said step (d) comprises treating said LL diastereomer salt with an optically inactive strong acid for the purpose of splitting off said N-acetyl-L-proline from L-carnitine nitrile salt and separating said N-acetyl-L-proline from said L-carnitine nitrile salt by using an organic solvent.

15. The process according to claim 1, wherein said step (e) comprises heating said L-carnitine nitrile salt with mineral acid and separating the anion of said mineral acid from the resulting L-carnitine salt.

16. The process according to claim 1, wherein said step (a) comprises treating said D,L-carnitine nitrile salt with a strongly basic ion exchanger to form said D,L-carnitine nitrile hydroxide.

* * * * *